(12) United States Patent
Liu et al.

(10) Patent No.: US 12,038,165 B2
(45) Date of Patent: Jul. 16, 2024

(54) LEAKPROOF STRUCTURE OF THE LAMP HOLDER OF THE INFRARED LAMP TUBE

(71) Applicants: Chen Ya Liu, Taoyuan (TW); Chin Yuan Liu, Taoyuan (TW)

(72) Inventors: Chen Ya Liu, Taoyuan (TW); Chin Yuan Liu, Taoyuan (TW)

(*) Notice: Subject to any disclaimer, the term of this patent is extended or adjusted under 35 U.S.C. 154(b) by 0 days.

(21) Appl. No.: 18/451,342

(22) Filed: Aug. 17, 2023

(65) Prior Publication Data
US 2024/0077195 A1 Mar. 7, 2024

(30) Foreign Application Priority Data
Sep. 6, 2022 (TW) .................................. 111209738

(51) Int. Cl.
| | | |
|---|---|---|
| *F21V 31/00* | (2006.01) | |
| *F21V 17/16* | (2006.01) | |
| *F21V 19/00* | (2006.01) | |
| *F21V 29/57* | (2015.01) | |
| *F21Y 103/10* | (2016.01) | |

(52) U.S. Cl.
CPC .......... *F21V 31/005* (2013.01); *F21V 17/164* (2013.01); *F21V 19/0005* (2013.01); *F21V 29/57* (2015.01); *F21Y 2103/10* (2016.08)

(58) Field of Classification Search
CPC .... F21V 31/005; F21V 19/0005; F21V 29/56; F21V 29/57
See application file for complete search history.

(56) References Cited

U.S. PATENT DOCUMENTS 9,316,387 B1 * 4/2016 Olsson ...................... F21V 5/04
2021/0356110 A1 * 11/2021 Zhang ................. F21V 19/0055

FOREIGN PATENT DOCUMENTS

| CN | 213991042 U | * | 8/2021 |
| TW | M610319 U | * | 4/2021 |

OTHER PUBLICATIONS

Machine translation of TW M610319U, Liu et al., published Apr. 11, 2021 (Year: 2021).*
Machine translation of CN 213991042U, Liu et al., published Aug. 17, 2021 (Year: 2021).*

* cited by examiner

*Primary Examiner* — William N Harris
(74) *Attorney, Agent, or Firm* — Rosenberg, Klein & Lee (57) ABSTRACT

A leakproof structure of the lamp holder, combined with an installation hole, which can ensure that the coolant in the accommodation space does not leak out; moreover, the lower part of the halogen bulb is covered by the waterproof plug in a tight state, so as to achieve a complete leakproof structure. Therefore, according to the temperature of the coolant, the automatic control system calculate the optimal flow rate of the coolant in a proportional mode that the higher the temperature, the faster the flow rate, so as to achieve the most effective mode of heat dissipation, then perform contact heat dissipation to the halogen bulb to solve the problem of the non-contact heat dissipation of halogen bulb of the prior art that cannot achieve the predetermined heat dissipation effect and resulting in the easy damage of halogen bulb; and further improves the product reliability and the service life.

6 Claims, 9 Drawing Sheets

LEAKPROOF STRUCTURE OF THE LAMP HOLDER OF THE INFRARED LAMP TUBE

BACKGROUND OF THE INVENTION

1. Field of the Invention

A leakproof structure of the lamp holder of the infrared lamp tube, especially one that has a lamp holder placed at the installation hole of the infrared lamp tube to achieve a leakproof structure.

2. Description of the Related Art

Infrared rays will penetrate into the depths of the human skin for 40 mm, by promoting the resonance of human cell molecules, charged and movement to expand the blood vessels, making blood circulation smooth and generate self-heating, and also increase the temperature of the deep body and improve metabolism, activate cell tissue, promote the excretion of toxins and wastes in the body and relieves fatigue. When the temperature of the body part increased, it can inhibit the proliferation of cancer cells and activate the immune system. As the body temperature rises with 1° C., the immune system is activated 5 to 6 times. Therefore, by increasing the temperature of the body part, it can relieve pain and prevent the proliferation of cancer cells, and activate the immune system to reduce cancer cells.

Taiwan Patent No. M610319, An infrared device with fluid heat dissipation, comprising: the body is a long body made of aluminum extrusion, and the section of the body is concave so that the two ends of the body form two concave end surfaces, and an accommodating space is formed inside the body, At least one fluid channel is provided between the concave end faces with the accommodating space as the center, and each halogen lamp is located in the accommodating space, so that the side position of each halogen lamp corresponds to the side position of the fluid channel, forming each There is a barrier between the halogen lamp and the fluid channel, and the filter is statically placed in the accommodating space; thereby, when the halogen lamp emits full-wavelength colored light through the filter, the color temperature of the full-wavelength colored light is changed, and the filter Infrared color light is emitted to the outside of the light guide plate, and is separated from the halogen lamp by a barrier with the fluid in the fluid channel, so that the fluid flows to perform non-contact heat dissipation on the halogen lamp.

However, although having non-contact heat dissipation, the working temperature of the halogen lamp is too high, non-contact heat dissipation for halogen lamps is not easy to achieve the desired heat dissipation effect, and after the high temperature of halogen lamps accumulating for a long time, it will greatly affect the service life and reliability of halogen lamps. However, to achieve contact heat dissipation on the halogen lamp, the problem of the infrared lamp tube and the lamp holder of the halogen lamp being prone to water leakage need to be solved.

Therefore, in view of the above-mentioned problems, the inventor conceived a leakproof structure of the lamp holder of the infrared lamp tube, which is the subject of the present invention.

SUMMARY OF THE INVENTION

A primary objective of the present invention is to provide a leakproof structure of the lamp holder of the infrared lamp tube, using the flowing coolant directly contact cool the halogen lamp, and calculate the optimal flow rate of the coolant in a proportional mode that the higher the temperature, the faster the flow rate, so as to achieve the most effective mode of heat dissipation, thereby improving product reliability and the service life.

In order to achieve the above objective, the present invention, including: an elongated housing, whose section is concave to form an accommodating space, the bottom of the elongated housing is provided with at least one installation hole; at least one lamp holder corresponding to the installation hole arranged at the bottom of the elongated housing; at least one halogen bulb arranged on the lamp holder, and the upper section of the halogen bulb protrudes into the accommodating space; a light-transmitting board arranged on the top of the elongated housing; two left and right covers arranged on the left and right sides of the elongated housing respectively, and a flow hole is provided on the two left and right covers relative to the accommodating space; wherein the installation hole of the elongated housing is a screw hole, and the lamp holder includes: a hollow seat, having a ring shaped body formed on the top thereof, a protruding thread body that can be locked in the installation hole is formed on the ring shaped body, a first through hole is formed in the protruding thread body, below the first through hole is connected with a second through hole with a larger diameter, and an internal screw thread is formed at the bottom of the second through hole; an O-ring washer, which is sleeved on the bottom of the outer peripheral edge of the protruding thread body, and is pressed against the bottom edge of the elongated housing by the ring shaped body; a waterproof plug, which is tightly placed in the second through hole, the upper part of the waterproof plug is provided with a receiving hole for the lower part of the halogen bulb to be embedded, and an electrical pin of the halogen bulb protrude out the bottom of the waterproof plug; and an internal nut, which is locked in an internal screw thread at the bottom of the second through hole, for pressing the upper part of the waterproof plug against the bottom edge surface of the first through hole, so that the first through hole forms a waterproof closed state, and the internal nut has a third through hole.

Also, the waterproof plug is made of elastic material, the receiving hole is matched with the shape of the lower part of the halogen bulb, so that it can be combined into a tight fit, and the bottom of the receiving hole is provided with two small perforations for letting the electrical pin of the halogen bulb protrude and locate in the third through hole.

Also, the left and right covers are further locked on both sides of the elongated housing by multiple screws, and the left and right covers further include a sealing gasket.

Also, the light-transmitting board further includes two joint strips respectively pressed and fixed on the front and rear sides of the light-transmitting board, so that the light-transmitting board is fixed on the top of the elongated housing.

Also, the light-transmitting board is composed of a light guide plate.

Also, the infrared lamp tube further includes an automatic control system for heat dissipation, and the automatic control system for heat dissipation includes: a circulation line, which includes an input end and an output end, respectively connected to the flow holes of the right and left covers, for injecting coolant into the accommodating space of the infrared lamp tube and circulating it, so as to cool down the halogen bulb.

With the features above disclosed, the leakproof structure of the lamp holder of the present invention makes the lamp holder combined with the installation hole, and has an excellent sealing effect, which can ensure that the coolant in the accommodation space does not leak out from the installation hole; moreover, the lower part of the halogen bulb is covered by the waterproof plug in a tight state, so as to achieve a complete leakproof structure. Therefore, according to the temperature of the coolant in the accommodating space, the automatic control system for heat dissipation calculate the optimal flow rate of the coolant in a proportional mode that the higher the temperature, the faster the flow rate, so as to achieve the most effective mode of heat dissipation, then perform contact heat dissipation to the halogen bulb, so as to solve the problem of the non-contact heat dissipation of halogen bulb of the prior art that cannot achieve the predetermined heat dissipation effect and resulting in the easy damage of halogen bulb; and further improves the product reliability and the service life.

DETAILED DESCRIPTION OF THE PREFERRED EMBODIMENT

Referring to FIGS. 1-9, the applicable embodiment of the leakproof structure of the lamp holder of the infrared lamp tube of the present invention, the infrared lamp tube 10 including: an elongated housing 11, whose section is concave to form an accommodating space 111, the bottom of the elongated housing 11 is provided with at least one installation hole 112; at least one lamp holder 12 corresponding to the installation hole 112 arranged at the bottom of the elongated housing 11; at least one halogen bulb 13 arranged on the lamp holder 12, and the upper section of the halogen bulb 13 protrudes into the accommodating space 111; a light-transmitting board 14 arranged on the top of the elongated housing 11.

Two left and right covers 16 arranged on the left and right sides of the elongated housing 11 respectively, and a flow hole 161 is provided on the two left and right covers 16 relative to the accommodating space 111.

Figure 1:
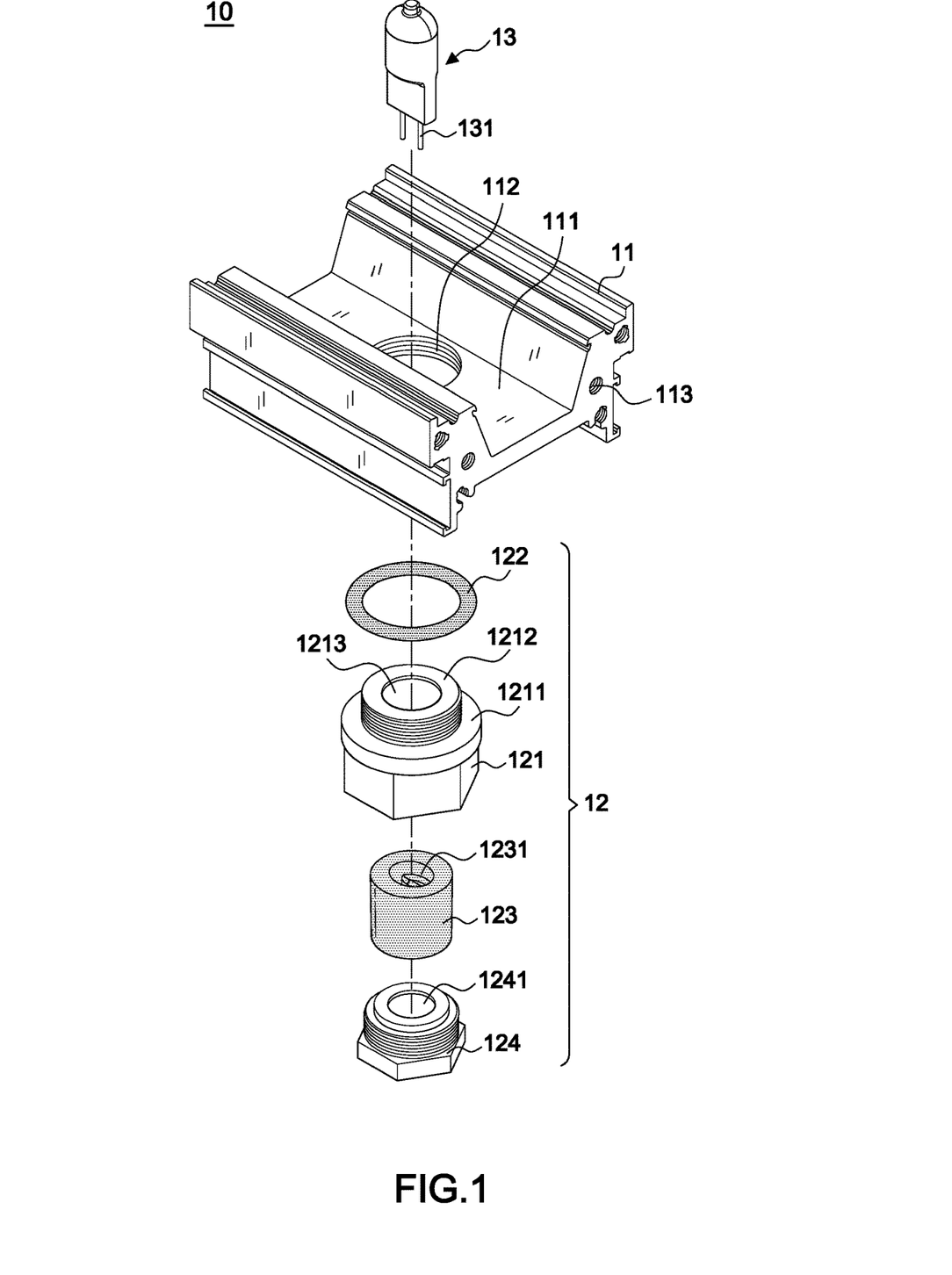
FIG. 1 is an exploded perspective view of the leakproof structure of the lamp holder of the present invention.
Figure 2:
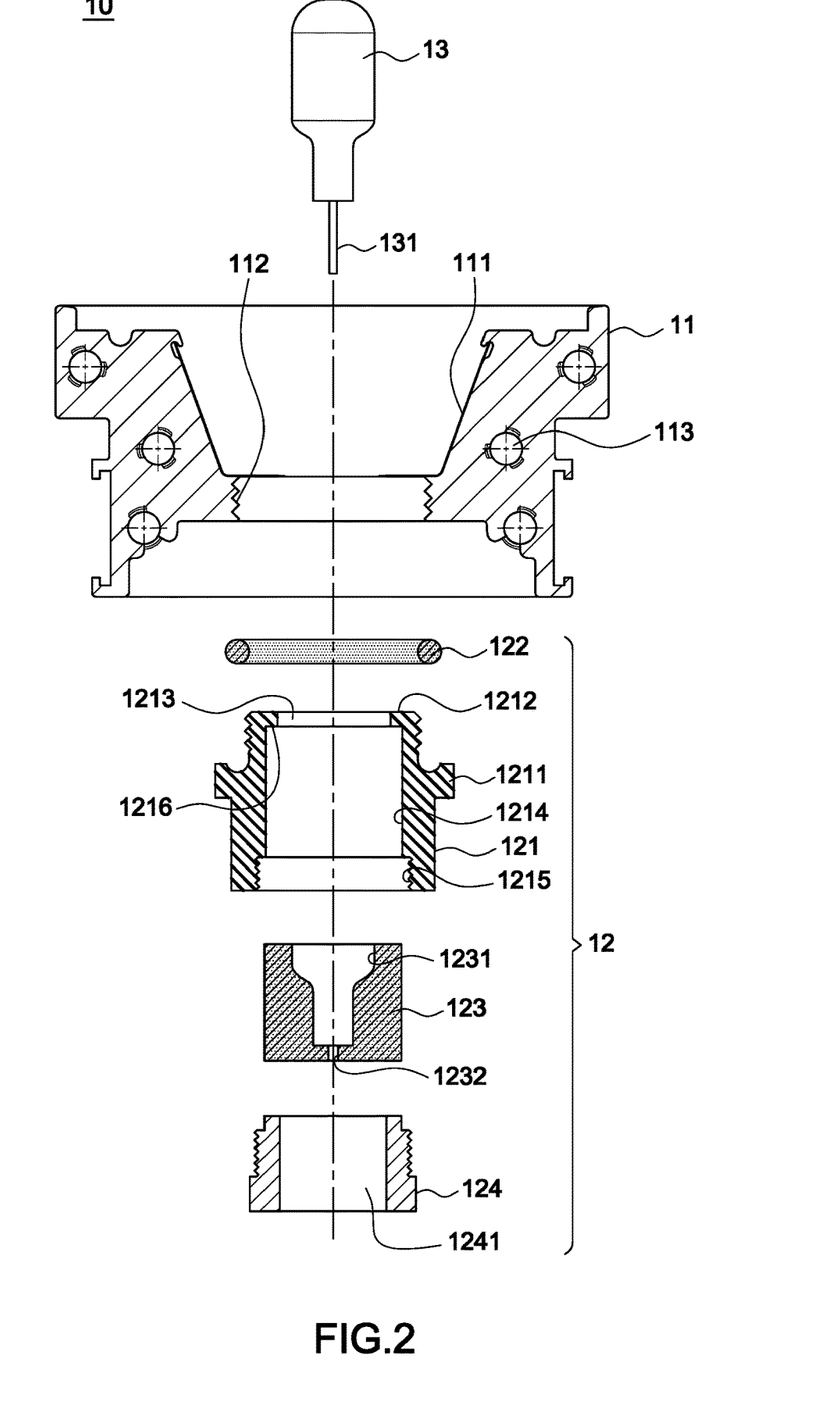
FIG. 2 is an exploded sectional view of the leakproof structure of the lamp holder of the present invention.
Figure 3:
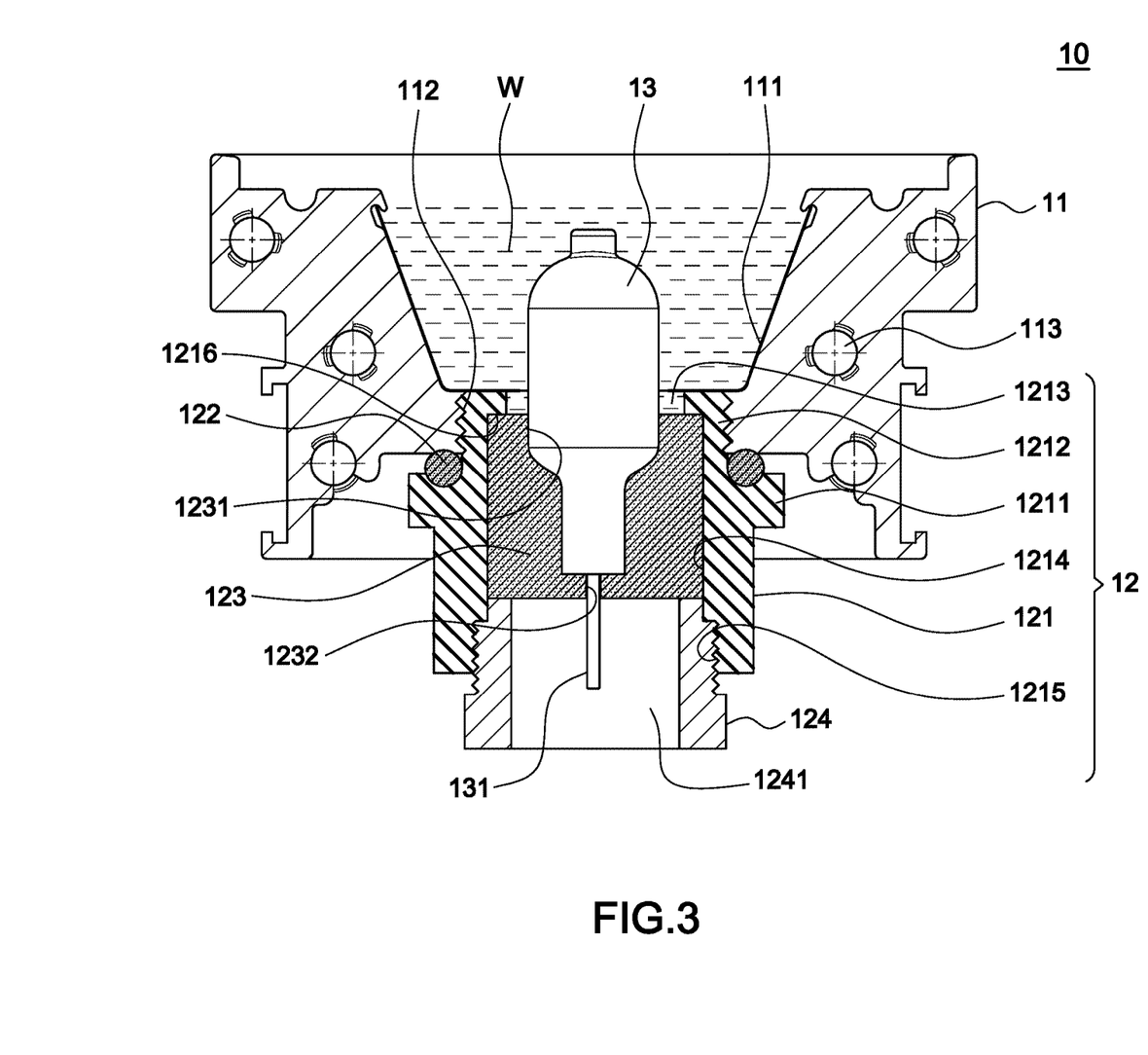
FIG. 3 is an assembly sectional view of the leakproof structure of the lamp holder of the present invention.

Referring to FIGS. 1-3, wherein the installation hole 112 of the elongated housing 11 is a screw hole, and the lamp holder 12 includes: a hollow seat 121, having a ring shaped body 1211 formed on the top thereof, a protruding thread body 1212 that can be locked in the installation hole 112 is formed on the ring shaped body 1211, a first through hole 1213 is formed in the protruding thread body 1212, below the first through hole 1213 is connected with a second through hole 1214 with a larger diameter, so as to form a stopping member 1216 below the first through hole 1213, and an internal screw thread 1215 is formed at the bottom of the second through hole 1214; an O-ring washer 122, which is sleeved on the bottom of the outer peripheral edge of the protruding thread body 1212, and is pressed against the bottom edge of the elongated housing 11 by the ring shaped body 1211; a waterproof plug 123, which is tightly placed in the second through hole 1214, the upper part of the waterproof plug 123 is provided with a receiving hole 1231 for the lower part of the halogen bulb 13 to be embedded, and an electrical pin 131 of the halogen bulb 13 protrude out the bottom of the waterproof plug 123; and an internal nut 124, which is locked in an internal screw thread 1215 at the bottom of the second through hole 1214, for pressing the upper part of the waterproof plug 123 against the bottom edge surface of the first through hole 1213, so that the first through hole 1213 forms a waterproof closed state, and the internal nut 124 has a third through hole 1241.

In this embodiment, the waterproof plug 123 is made of elastic material, the receiving hole 1231 is matched with the shape of the lower part of the halogen bulb 13, so that it can be combined into a tight fit, and the bottom of the receiving hole 1231 is provided with two small perforations 1232 for letting the electrical pin 131 of the halogen bulb 13 protrude and locate in the third through hole 1241.

With the structure disclosed above, the leakproof structure of the halogen bulb 13 of the present invention, as shown in FIG. 3, firstly, the O-ring washer 122 is sleeved on the bottom of the outer peripheral edge of the protruding thread body 1212, and is pressed against the bottom edge of the elongated housing 11 by the ring shaped body 1211, so that the lamp holder 12 is combined with the installation hole 112, and has an excellent sealing effect, which can ensure that the coolant W in the accommodating space 111 will not leaks out from the installation hole 112; moreover, the lower section of the halogen bulb 13 is covered by the waterproof plug 123 in a tight state, and the bottom of the waterproof plug 123 is pressed upward by the internal nut 124, making the top of the waterproof plug 123 against the stopping member 1216 of the first through hole 1213 so that the first through hole 1213 forms a waterproof closed state; in this way, the present invention achieves a complete leakproof structure.

Figure 4:
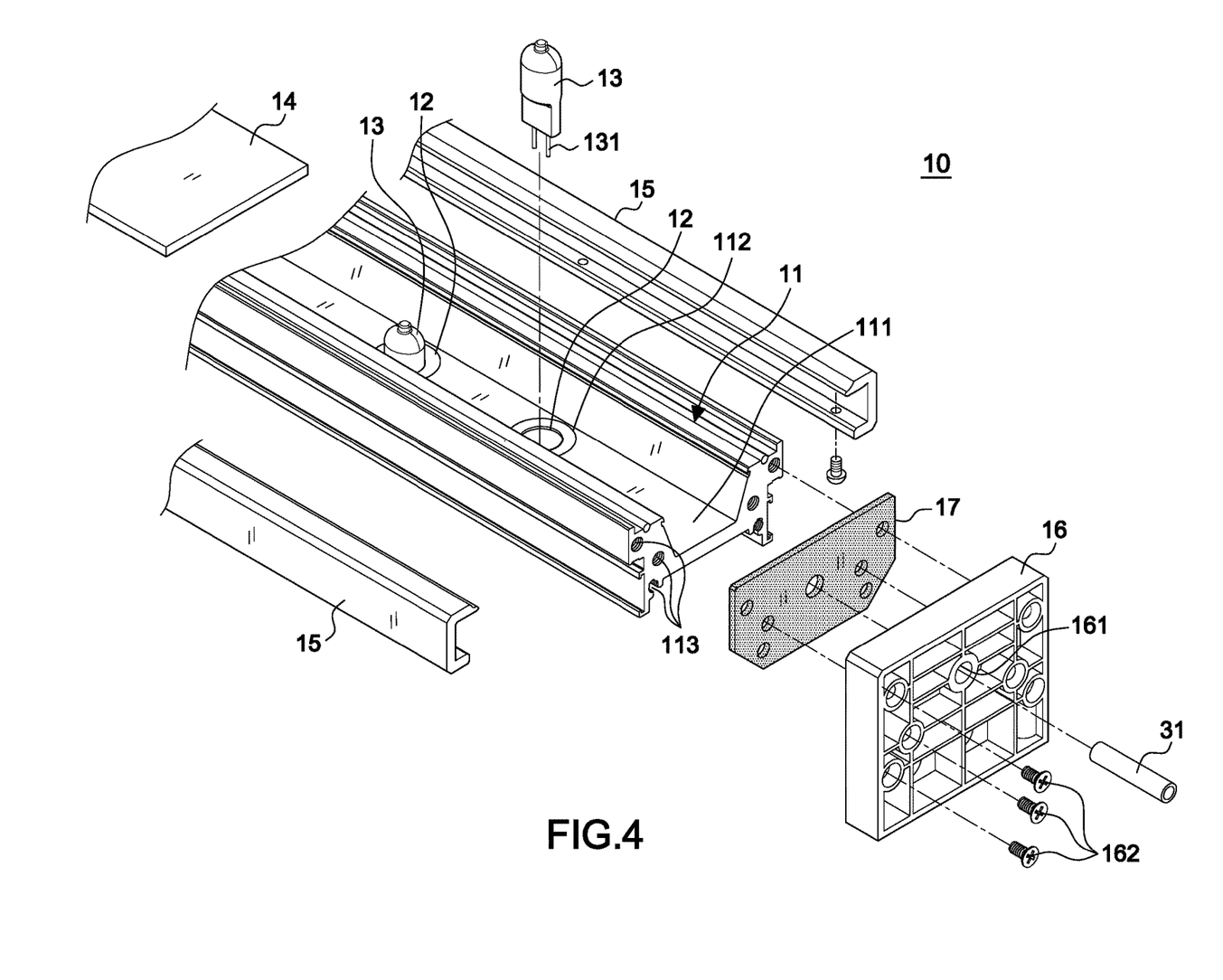
FIG. 4 is an exploded perspective view of the structure of the infrared lamp tube of the present invention.
Figure 5:
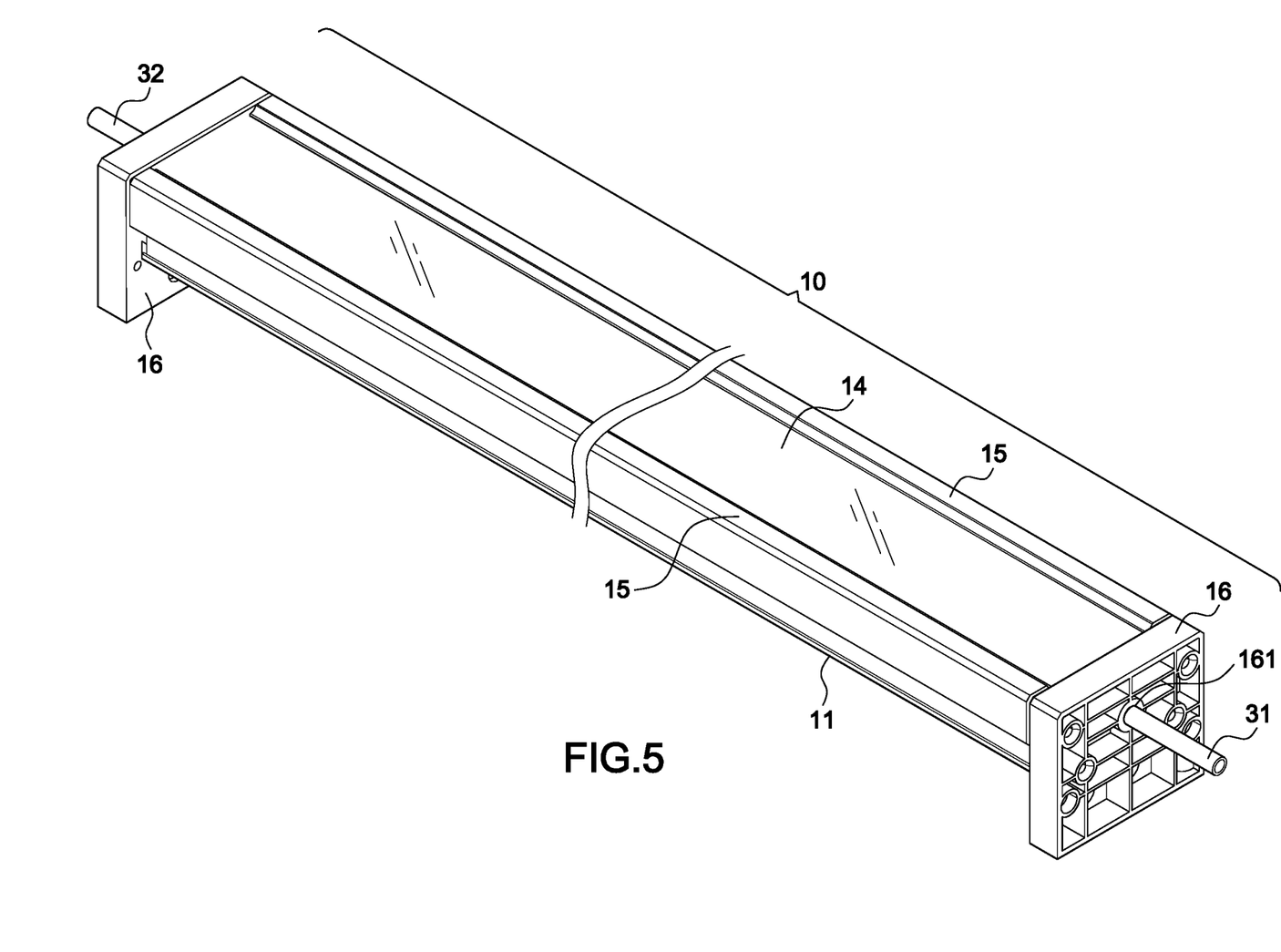
FIG. 5 is a top perspective view of the infrared lamp tube of an applicable embodiment of the present invention.
Figure 6:
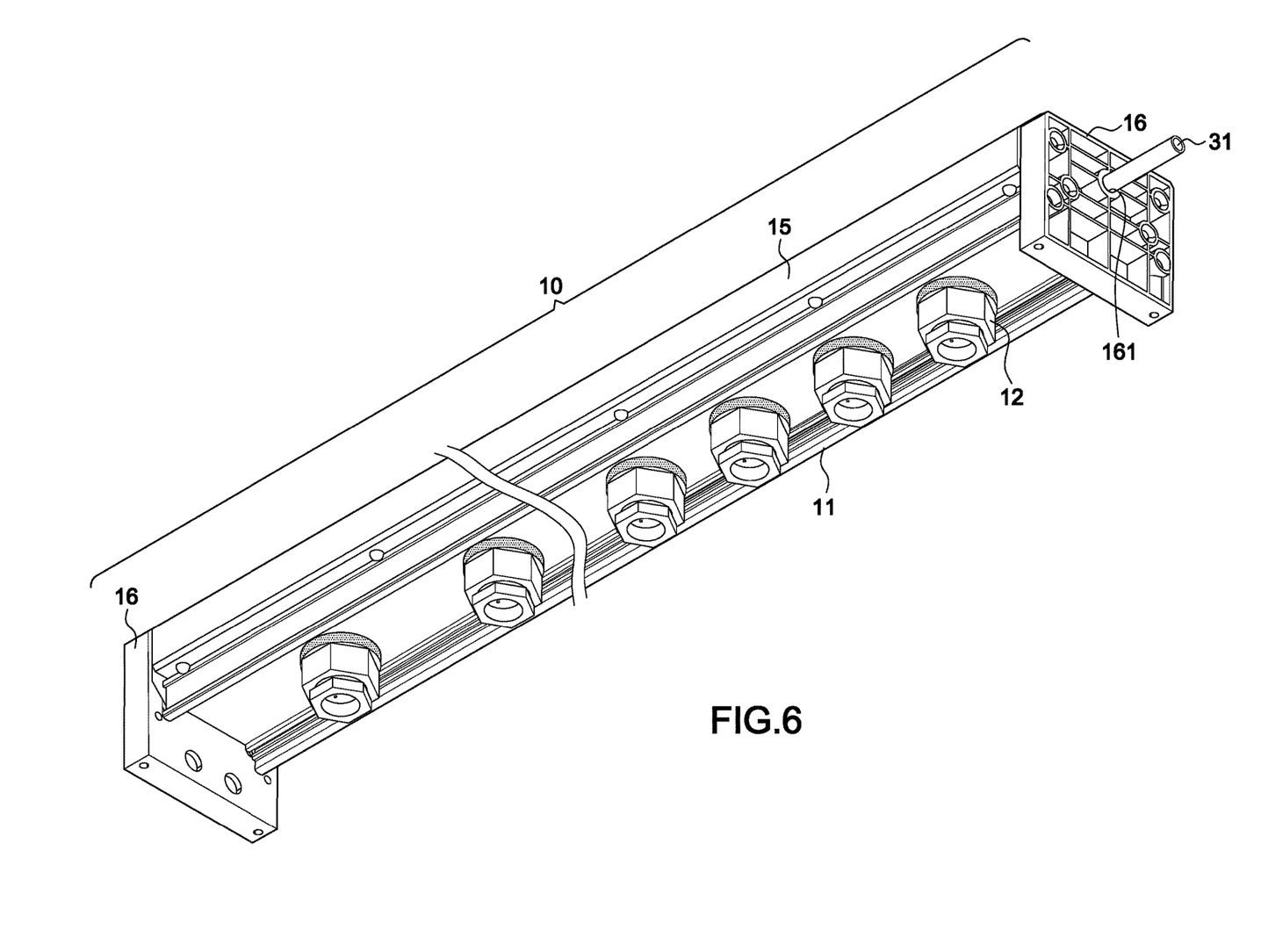
FIG. 6 is a bottom perspective view of the infrared lamp tube of an applicable embodiment of the present invention.
Figure 7:
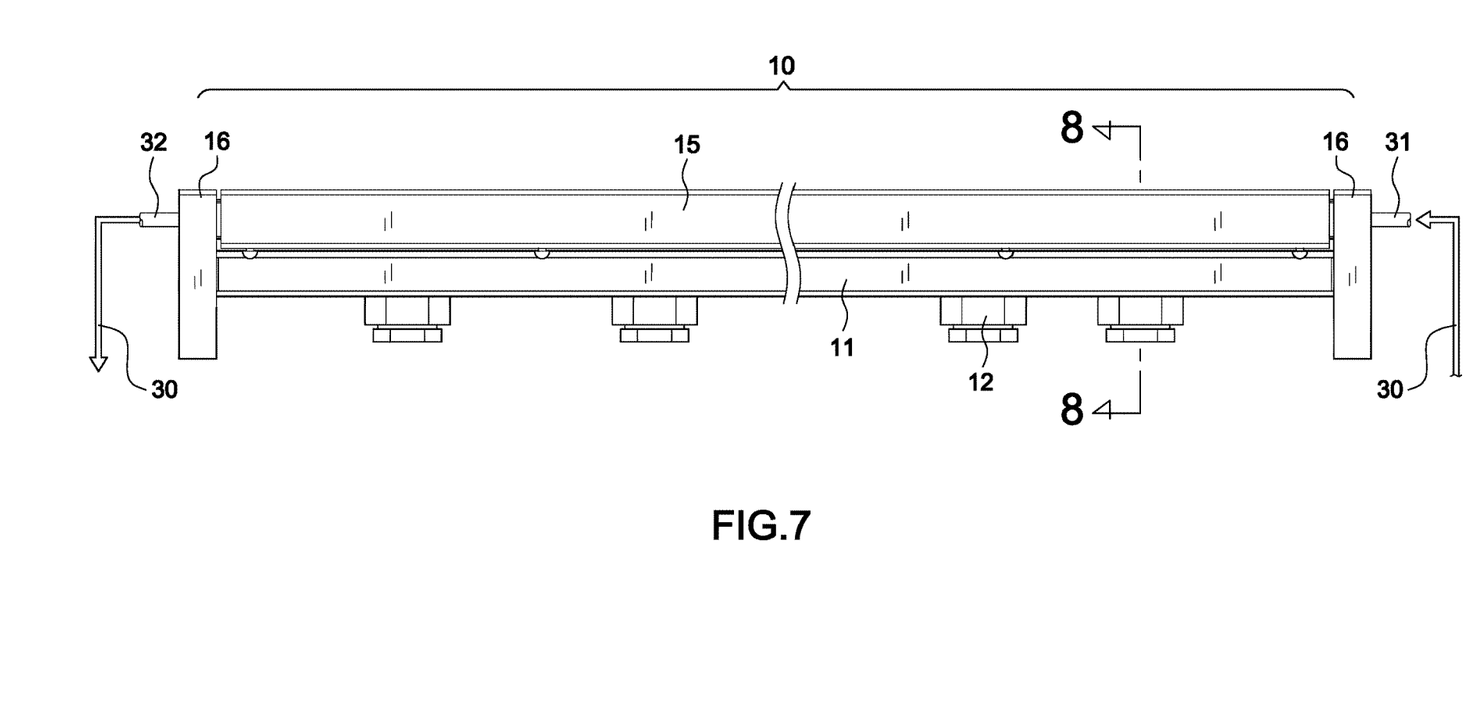
FIG. 7 is a side view of the infrared lamp tube of an applicable embodiment of the present invention.
Figure 8:
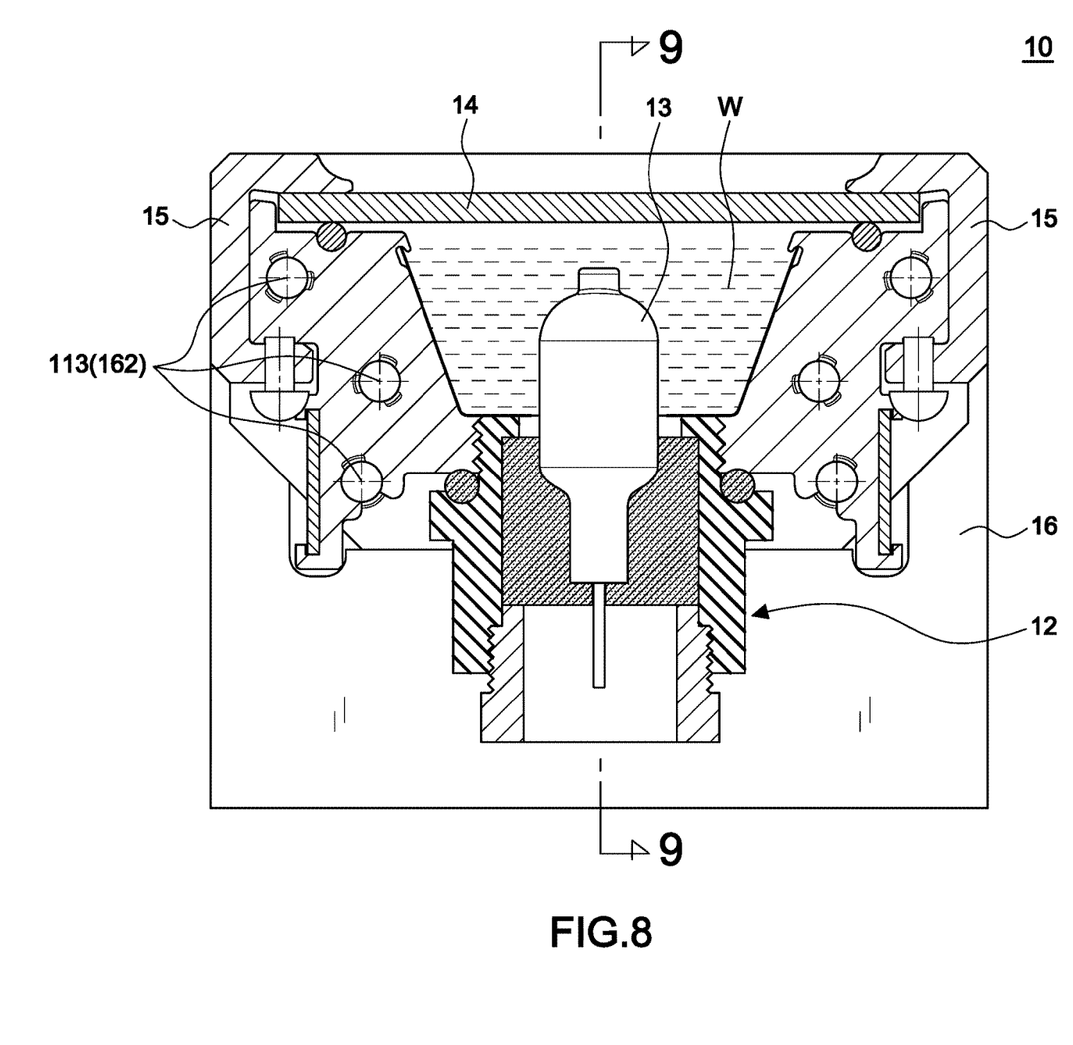
FIG. 8 is a sectional view along line 8-8 in FIG. 7.

FIG. 4 is an exploded perspective view of the structure of the infrared lamp tube of the present invention, with the leakproof structure of the lamp holder disclosed above, the present invention can achieve an embodiment of providing a leakproof infrared lamp tube; FIGS. 5-9 are perspective view of the infrared lamp tube of an applicable embodiment of the present invention; in this embodiment, the light-transmitting board 14 can be composed of a light guide plate and further includes two joint strips 15 respectively pressed and fixed on the front and rear sides of the light-transmitting board 14, so that the light-transmitting board 14 is fixed on the top of the elongated housing 11. The left and right covers 16 are further locked on a fixing hole 113 of both sides of the elongated housing 11 by multiple screws 162, and the inner side of the left and right covers 16 further include a sealing gasket 17, but not limited to this.

Figure 9:
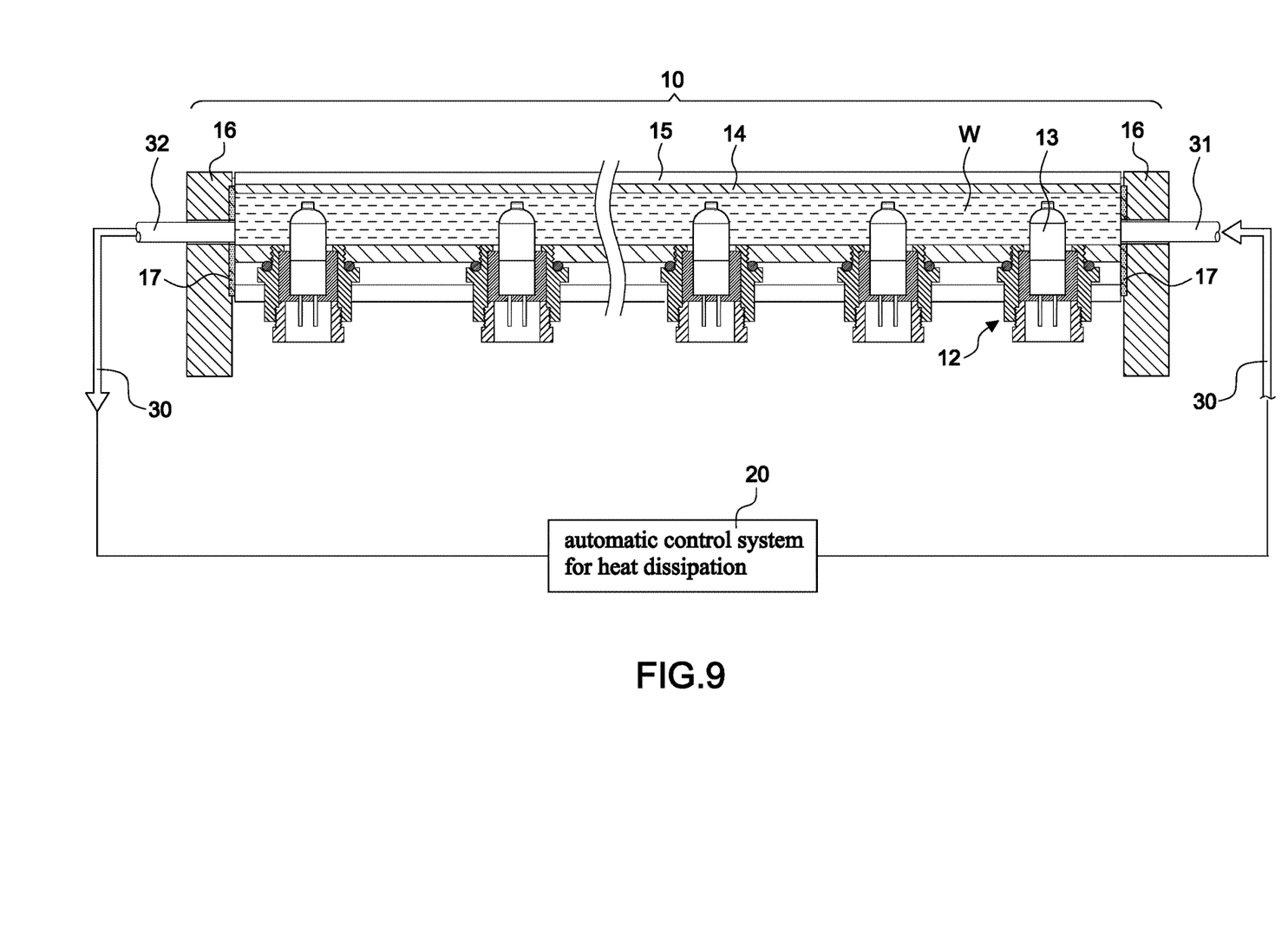
FIG. 9 is a sectional view along line 9-9 in FIG. 8.

Referring to FIG. 9, the infrared lamp tube 10 further includes an automatic control system for heat dissipation 20, and the automatic control system for heat dissipation 20 includes: a circulation line 30, which includes an input end 31 and an output end 32, respectively connected to the flow holes 161 of the right and left covers 16, for injecting coolant W into the accommodation space 111 of the infrared lamp tube 10 and circulating it, so as to cool down the halogen bulb 13; according to the temperature of the coolant W in the accommodating space 111, the automatic control system for heat dissipation 20 calculate the optimal flow rate of the coolant W in a proportional mode that the higher the temperature, the faster the flow rate, so as to achieve the most effective mode of heat dissipation, then perform contact heat dissipation to the halogen bulb 13, so as to solve the problem of the non-contact heat dissipation of halogen bulb of the prior art that cannot achieve the predetermined heat dissipation effect and resulting in the easy damage of halogen bulb; and further improves the product reliability and the service life.

The present invention uses contact heat dissipation for the halogen bulb 13 and controls the flow rate of the coolant W entering and leaving the accommodating space 111, the waterproof structure of the lamp holder 12 becomes very important to prevent the coolant W from leakage. If the leakage of the coolant W happened, then the infrared lamp tube 10 of the present invention cannot be achieved, so this structure becomes important.

With the features above disclosed, the leakproof structure of the lamp holder of the present invention makes the lamp holder 12 combined with the installation hole 112, and has an excellent sealing effect, which can ensure that the coolant W in the accommodation space 111 does not leak out from the installation hole; moreover, the lower part of the halogen bulb 13 is covered by the waterproof plug 123 in a tight state, so as to achieve a complete leakproof structure. Therefore, solve the problem of the non-contact heat dissipation of halogen bulb of the prior art that cannot achieve the predetermined heat dissipation effect and resulting in the easy damage of halogen bulb; and further improves the product reliability and the service life.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A leakproof structure of a lamp holder of an infrared lamp tube, including:
    an elongated housing, whose section is concave to form an accommodating space, a bottom of the elongated housing is provided with at least one installation hole;
    at least one lamp holder corresponding to the at least one installation hole arranged at the bottom of the elongated housing;
    at least one halogen bulb arranged on the lamp holder, and an upper section of the halogen bulb protrudes into the accommodating space;
    a light-transmitting board arranged on a top of the elongated housing;
    two left and right covers arranged on left and right sides of the elongated housing respectively, and a flow hole is provided on the two left and right covers relative to the accommodating space;
    wherein the at least one installation hole of the elongated housing is a screw hole, and the lamp holder includes:
    a hollow seat, having a ring shaped body formed on the top thereof, a protruding thread body that can be locked in the installation hole is formed on the ring shaped body, a first through hole is formed in the protruding thread body, the first through hole is connected with a second through hole with a larger diameter located below the first through hole, and an internal screw thread is formed at a bottom of the second through hole;
    an O-ring washer, which is sleeved on a bottom of the outer peripheral edge of the protruding thread body, and is pressed against a bottom edge of the elongated housing by the ring shaped body;
    a waterproof plug, which is tightly placed in the second through hole, an upper part of the waterproof plug is provided with a receiving hole for a lower part of the halogen bulb to be embedded, and an electrical pins of the halogen bulb protrude out of a bottom of the waterproof plug; and
    an internal nut, which is locked in the internal screw thread at the bottom of the second through hole, for pressing the upper part of the waterproof plug against an bottom edge surface of the first through hole, so that the first through hole forms a waterproof closed state, and the internal nut has a third through hole.

2. The leakproof structure as claimed in claim 1, wherein the waterproof plug is made of elastic material, the receiving hole is matched with the shape of the lower part of the halogen bulb, so that the waterproof plug and the lower part of the halogen bulb can be combined into a tight fit, and a bottom of the receiving hole is provided with two perforations for passage of the electrical pins of the halogen bulb therethrough and into the third through hole.

3. The leakproof structure as claimed in claim 1, wherein the left and right covers are further locked on both sides of the elongated housing by multiple screws, and the left and right covers further include a sealing gasket.

4. The leakproof structure as claimed in claim 1, wherein the light-transmitting board further includes front and rear sides, and two joint strips respectively pressed and fixed on the front and rear sides of the light-transmitting board, so that the light-transmitting board is fixed on the top of the elongated housing.

5. The leakproof structure as claimed in claim 1, wherein the light-transmitting board is composed of a light guide plate.

6. The leakproof structure as claimed in claim 1, wherein the infrared lamp tube further includes an automatic control system for heat dissipation, and the automatic control system for heat dissipation includes: a circulation line, which includes an input end and an output end, respectively connected to the flow holes of the right and left covers, for injecting coolant into the accommodating space of the infrared lamp tube and circulating the coolant, so as to cool down the halogen bulb.

* * * * *